US006077221A

United States Patent [19]
Fowler, Jr.

[11] Patent Number: 6,077,221
[45] Date of Patent: Jun. 20, 2000

[54] SURGICAL RESTRAINT SYSTEM

[75] Inventor: James M. Fowler, Jr., Houston, Tex.

[73] Assignee: Lone Star Medical Products, Inc., Houston, Tex.

[21] Appl. No.: 09/388,119

[22] Filed: Sep. 1, 1999

[51] Int. Cl.⁷ .................................................. A61B 17/02
[52] U.S. Cl. ........................... 600/233; 434/262; 600/227
[58] Field of Search .................................... 600/231, 233, 600/232, 227; 434/268, 272, 262, 267

[56] References Cited

U.S. PATENT DOCUMENTS

| | | | |
|---|---|---|---|
| Re. 32,021 | 11/1985 | Scott, Jr. ................................... | 128/20 |
| 2,612,891 | 10/1952 | Smith ..................................... | 600/235 |
| 2,845,925 | 8/1958 | Jayle ..................................... | 600/233 |
| 3,515,129 | 6/1970 | Truhan ................................... | 128/20 |
| 3,542,015 | 11/1970 | Steinman ................................ | 128/20 |
| 3,762,401 | 10/1973 | Tupper ................................... | 600/227 |
| 3,916,879 | 11/1975 | Cotten ................................... | 128/12 |
| 3,970,075 | 7/1976 | Sindelar et al. ......................... | 600/231 |
| 4,001,952 | 1/1977 | Kleppinger .............................. | 434/262 |
| 4,048,987 | 9/1977 | Hurson ................................... | 128/20 |
| 4,185,636 | 1/1980 | Gabbay et al. ..................... | 128/334 R |
| 4,254,763 | 3/1981 | McCready et al. ...................... | 128/20 |
| 4,274,398 | 6/1981 | Scott, Jr. ................................. | 128/20 |
| 4,337,762 | 7/1982 | Gauthier ................................. | 128/20 |
| 4,355,631 | 10/1982 | LeVahn .................................. | 128/20 |
| 4,380,999 | 4/1983 | Healy ..................................... | 128/20 |
| 4,421,107 | 12/1983 | Estes et al. .............................. | 128/20 |
| 4,421,108 | 12/1983 | Cabrera et al. ......................... | 128/20 |
| 4,430,991 | 2/1984 | Darnell ................................... | 128/20 |
| 4,434,791 | 3/1984 | Darnell ................................... | 128/20 |
| 4,559,677 | 12/1985 | Tracy ..................................... | 24/300 |
| 5,231,974 | 8/1993 | Giglio et al. ............................ | 128/20 |
| 5,769,783 | 6/1998 | Fowler ................................... | 600/226 |
| 5,785,649 | 7/1998 | Fowler, Jr. ............................. | 600/233 |

FOREIGN PATENT DOCUMENTS

| | | |
|---|---|---|
| 1222141 | 2/1971 | United Kingdom . |
| 1550254 | 8/1979 | United Kingdom . |
| 1550255 | 8/1979 | United Kingdom . |

OTHER PUBLICATIONS

Aesculap®, Bone Retractors and Retractors, Product catalog, pp. 319–320 (2 pages).
MD&M Review, Thermoplastic Replaces Metal in Disposable Abdominal Retractor, ULTOP® Conveyor Modules (1 page).
I.S.I. North America, Inc. *International Surgical Instruments* Brochure (1 page).
Accurate Surgical & Scientific Instruments Corporation Brochure, Tupper's Universal Handholder and Retraction Set®, p. 39 (1 page).

*Primary Examiner*—Paul J. Hirsch
*Attorney, Agent, or Firm*—Akin, Gump, Strauss, Hauer & Feld, L.L.P.

[57] ABSTRACT

A retractor system having a tray for receiving a small animal or a portion of a body during surgery. The tray has a notched flange for receiving an elastic member of a surgical stay while a tissue holding member of the stay holds a surgical incision open. The tray also includes a drain and a spout either of which may be used to discharge fluids accumulating during surgery. The system may include a snap-on cover to contain the tray contents when moving the tray. The system may have an inclined, textured bottom member and wall holes for receiving adjustable arms having notched flanges.

37 Claims, 5 Drawing Sheets

SURGICAL RESTRAINT SYSTEM

CROSS-REFERENCE TO RELATED APPLICATIONS

Not applicable.

STATEMENT REGARDING FEDERALLY SPONSORED RESEARCH

Not applicable.

BACKGROUND OF THE INVENTION

1. Field of the Invention

The present invention relates to a tray for use in surgery, particularly hand or foot surgery or on small animals. More particularly, the present invention relates to an improved tray with a drain, a notched flange and, optionally, flanged arms having notches for use with surgical retractor stays.

2. Description of the Related Art

During the course of a surgical procedure or operation, the surgeon opens the patient with a scalpel, forming an incision and surgical site. The surgical incision is a source of body fluids which may drain into the surgical field. Also, irrigation of the incision is another source of surgical fluids which may drain into the surgical field. The body and irrigation fluids are generally treated as if they contain pathogenic species and must be disposed of in a manner which reduces potential exposure of personnel to the fluids.

As the surgeon cuts deeper, the operating room staff typically holds tissue away from the operative field using retractors. Portions of the body, such as hands or feet, may be placed on a pallet or table to immobilize the body part while allowing the incision to be held open through the use of surgical stays. U.S. Pat. No. 3,762,401 discloses such a restraint. While this restraint holds the incision open during surgery, the restraint of U.S. Pat. No. 3,762,401 does not prevent body fluids or irrigation fluids from contaminating the surgical field.

There exists a need for an improved retractor surgical system which permits the safe accumulation of body fluids and irrigation fluids associated with surgical or dissection procedures while also holding the incision open and immobilizing the surgical site.

There exists a need for an improved retractor surgical system for use with small, live animals which permits the safe accumulation of body fluids and irrigation fluids associated with surgical procedures, while also holding an incision open and immobilizing the animal.

SUMMARY OF THE INVENTION

The present invention provides an improved surgical restraint system that offers several benefits over the prior art. The containment and collection of body fluids and irrigation fluids during surgery is accomplished with the surgical restraint system of the present invention. The surgical restraint system may be used with humans or animals.

The surgical restraint system provides a tray for immobilizing a body part during surgery while permitting collection of body fluids and irrigation fluids during surgery to minimize contamination of the surgical field and to reduce exposure of surgical personnel to the fluids. The body part on which surgery is to be performed is received in the tray and a notched flange on the tray is adapted to receive a portion of a restraint used to immobilize the body part or hold a surgical incision open.

The present invention may also provide a drain in the tray for removal of fluids collected during surgery.

The tray flange may also include a spout to aid pouring the collected fluids into a suitable disposal container.

The present invention further provides a snap-on lid to reduce the introduction of foreign materials into the apparatus prior to use and to safely contain the fluids collected during surgery if the tray must be moved to another site for disposal of the fluids.

One embodiment of the present invention is a restraint system for use during surgery having a tray with a notched flange, a drain, a spout and a surgical stay having an elongated member and a tissue holding member attached to the elongated member.

One embodiment of the restraint system according to the present invention includes an insert in the tray for receiving immobilizing devices such as pins or needles during dissection of laboratory specimens.

One embodiment of the present invention is a restraint system for use during dissection having a tray with a notched flange, a drain, a spout, an insert for receiving immobilizing devices and a surgical stay having an elongated member and a tissue holding member attached to the elongated member.

In yet another embodiment, the surgical restraint system provides a tray with a textured, sloping bottom member which aids draining fluids and positioning an animal. The tray is adapted to receive adjustable arms. The tray and arms each have notched flanges adapted to receive an elongated member of a restraint or stay to immobilize the animal or hold an incision open.

The tray flange or wall may also include an opening to receive an electrical cable for a heating pad used with the tray. The opening may also serve as a spout to aid pouring accumulated fluids into a suitable disposal container.

Another embodiment of the present invention is a surgical restraint system for use during live animal surgery having a tray with a notched flange, adjustable arms having notched flanges, a drain, a sloped, textured floor and a surgical retractor stay having an elongated member with a tissue holding member attached to the elongated member.

BRIEF DESCRIPTION OF THE DRAWINGS

For a further understanding of the nature, objects and advantages of the present invention, reference should be made to the following detailed description, read in conjunction with the following drawings, wherein like reference numerals indicate like elements and wherein.

DETAILED DESCRIPTION OF INVENTION

The surgical restraint system of the present invention, generally referred to as S, is shown in FIGS. 1–5. The surgical restraint system S includes a tray 10 adapted to receive a portion of a body, referred to as B, for example a hand (FIGS. 1 and 4) or foot. The tray 10 has a bottom member 12 from which a wall 14 extends to form a well to receive the body portion B and fluids associated with surgery or dissection. The bottom member 12 typically has a peripheral edge from which the peripheral wall 14 extends to form a square or rectangular well in tray 10. Alternatively, the bottom member 12 may be round having a wall 14 forming a round well in the tray 10. It is to be understood that the bottom member 12 can be various other shapes including, but not limited to, oval and elliptical. Also, the bottom member 12 may have a textured floor having a roughened surface including, but not limited to, a series of ridges or raised portions of the bottom surface for reducing movement of the animal or portion of the body received by tray 10. Although the wall 14 is shown as being substantially vertical and planar, it is to be understood that the wall 14 may alternatively be curved and non-planar.

Figure 1:
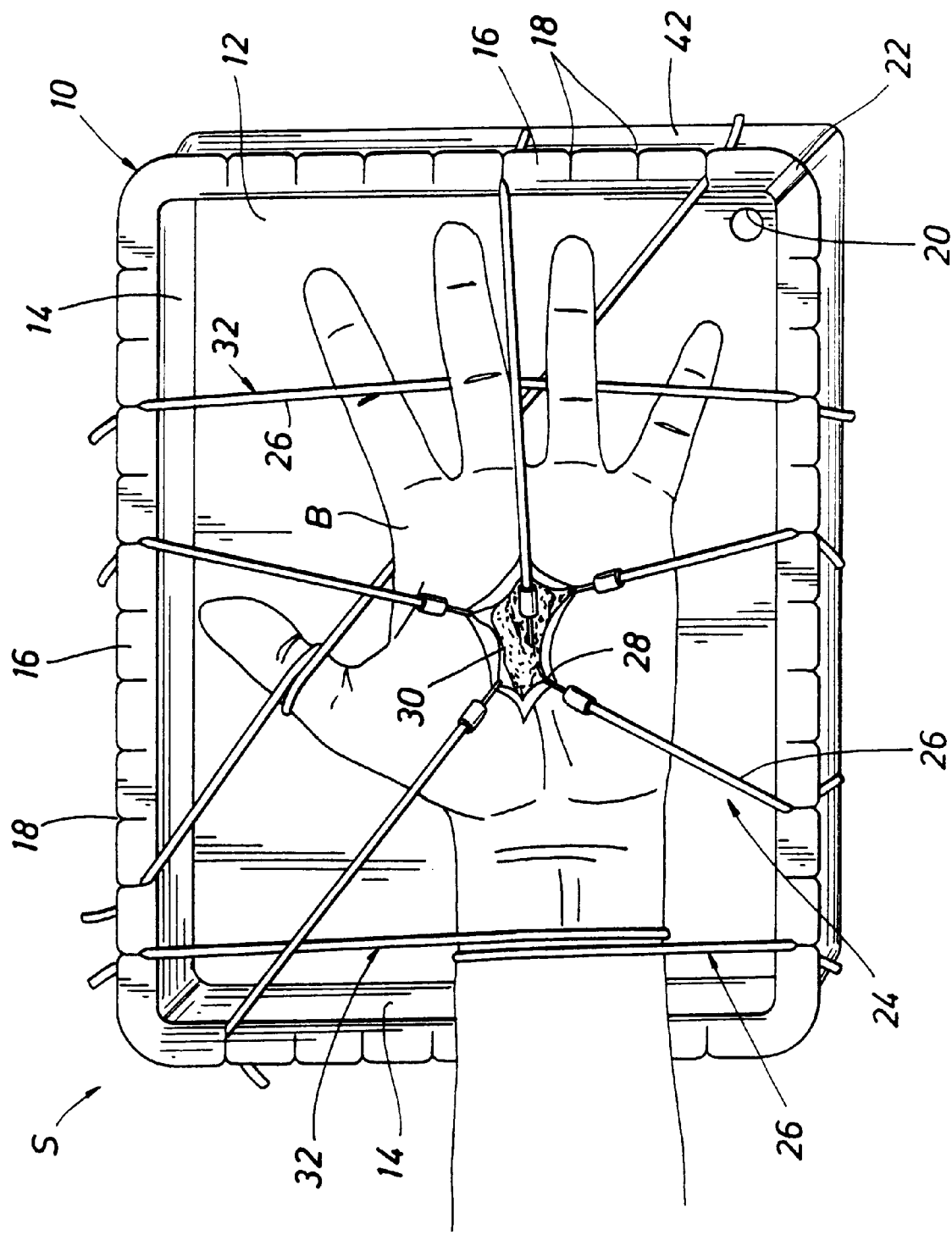
FIG. 1 is a perspective view of a restraint system restraining a hand during a surgical procedure.

Referring to FIG. 1, a flange 16 extends from an upper perimeter the wall 14. The flange 16 contains a plurality of notches 18 which are adapted to receive an elongated member 26 of a surgical retractor stay 24 or of a restraint stay 32. The flange 16 typically has a low profile structure which may be concave to increase the accessibility of the stays 24 for ease of placement.

The elongated member 26 of the surgical retractor stay 24 or the restraint stay 32 may be an elastic member of uniform diameter as disclosed in U.S. Pat. Nos. 5,785,649; 5,769,783; Re. 32,021; and U.S. Ser. No. 09/067,125, filed Apr. 27, 1999 which are fully incorporated herein by reference. Alternatively, the elongated member 26 may be a non-elastic member, including but not limited to, a ball and link member as disclosed in U.S. Pat. No. 3,762,401 which is fully incorporated herein by reference. The elongated member 26 may have a non-uniform diameter along its length, instead having spaced apart, enlarged diameter sections such as disclosed in U.S. Pat. No. 5,785,649 which is fully incorporated by reference. Alternatively, the elongated member 26 may be a ribbed elastic member.

The notches 18 are typically tapered toward the wall 14 and are generally less than the width of the elongated member 26 to retain the retractor stay 24 or the restraint stay 32 in the notch 18 by friction. Alternatively, the notches 18 may be wider than the elongated member 26 as, for example, when the elongated member 26 has enlarged diameter sections such as disclosed in U.S. Pat. No. 5,785,649 or when the stay 24, 32 has a ball and link member such as disclosed in U.S. Pat. No. 3,762,401. The enlarged diameter sections prevent the elongated members 26 from slipping through the notch 18.

The elongated member 26 is held in place by the notch 18 but may be easily removed at the end of a surgical procedure. The elongated member may be easily removed during a surgical procedure or adjusted or inserted into a different notch to adjust the tension of the stay 24, 32.

As shown in FIG. 1, the restraint stay 32, which may typically be elastic, acts as a physical restraint without using a hook member 28. The restraint 32 is typically wrapped around or placed over a body part to immobilize the body part. End portions of the restraint stay 32 are inserted into two notches 18, typically on opposing portions of the flange 16. Alternatively, surgical retractor stays 24 are used to hold an incision open. The hook member 28 of stay 24 is inserted into tissue around the incision and the elongated member 26 is adjusted to a desired tension and inserted into a notch 18 to retain the tissue in the desired retraction position.

As shown in FIG. 1, the well of tray 10 preferably has a drain opening 20. The opening 20 may be connected by any conventional method, for example by tubing, to a collection container (not shown) for receiving the fluids accumulating during surgery. The fluids typically include blood from the incision and fluids used to irrigate the surgical site before, during or after the surgery.

Alternatively, the drain opening 20 may be closed during the accumulation of the fluids when a relatively small amount of fluid is expected to be collected. The use of a spout 22, which may typically be integrally formed in a portion of flange 16, will aid in the transfer of the fluids from the well of the tray 10 into an appropriate storage and disposal container for potentially hazardous body fluids with a reduced risk of spilling the fluids.

Figure 2:
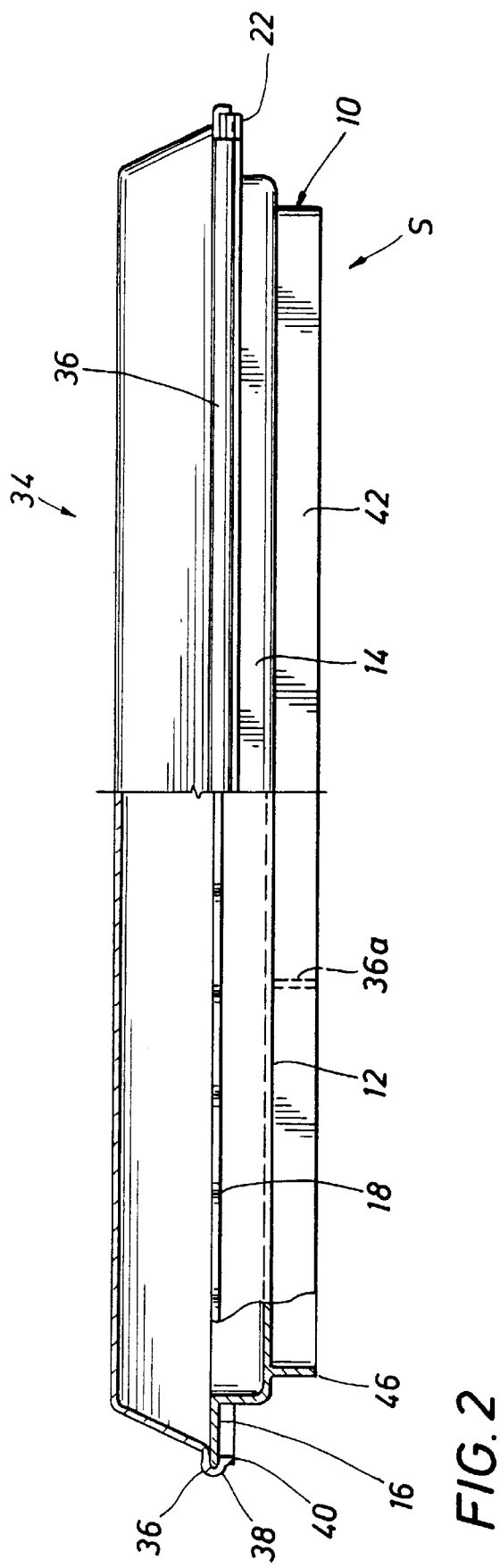
FIG. 2 is a side elevational view, with a partial sectional view, of a restraint system having a snap-on cap.

As shown in FIG. 2, the surgical restraint system S includes a snap-on cover 34 for the tray 10. The cover 34 has a wrap-around lip 36 which has a recess 38 for receiving the flange 16. The cover 34 reduces the potential for contamination of the interior and contents of tray 10 prior to surgery and also reduces potential spillage of accumulated fluids in the well of tray 10, when the drain opening 20 is closed during a surgical procedure, if the tray 34 must be moved out of the surgical field.

Figure 3:
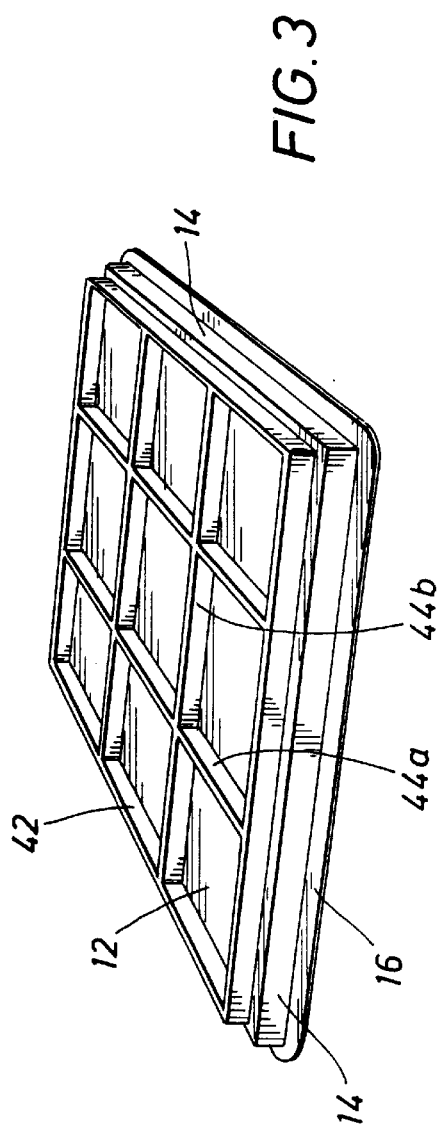
FIG. 3 is a perspective view of the bottom side of the surgical restraint system.

As shown in FIG. 3, the bottom surface of the tray 10 may have a ridge or rib 42 of material which is typically approximately the same dimensions as the perimeter of the tray 10. The rib 42 provides increased structural rigidity to the tray 10, particularly when used in conjunction with longitudinal ribs 44a and/or transverse ribs 44b.

Figure 4:
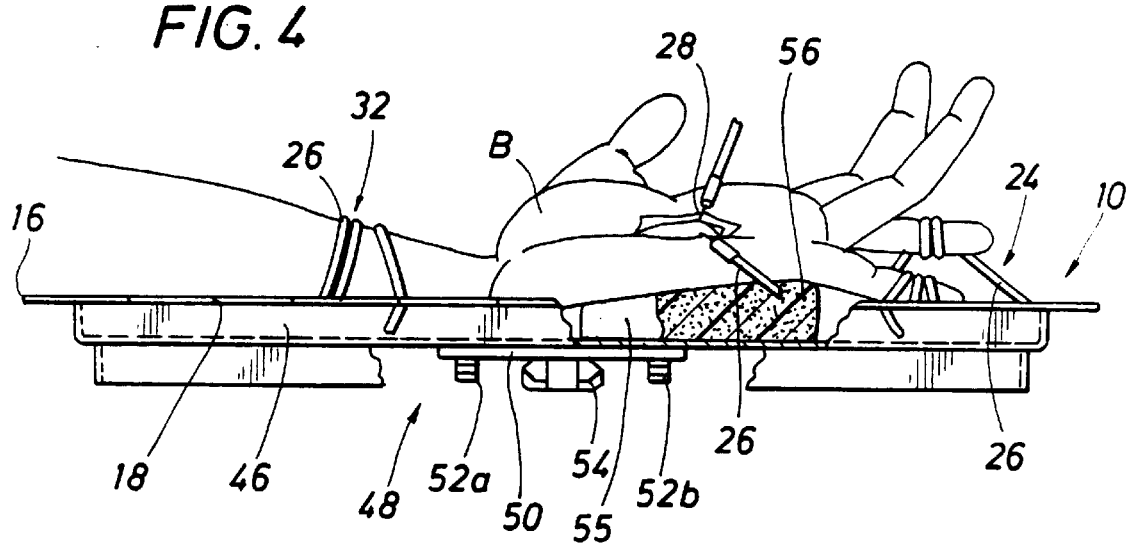
FIG. 4 is a side elevational view of a surgical restraint system with a support wedge.

As shown in FIG. 4, in addition to the use of the stays 24 to maintain easy access to the incision, the use of a support wedge 56 aids in maintaining the body part in a position which increases visibility and ease of access into the surgical incision. The wedge 56 may be provided in alternate preformed shapes to help reduce surgical time. Alternatively, the wedge 56 may be formed into customized shapes by the surgeon to fit specific needs encountered during surgery. The wedge 56 may be constructed from any material with sufficient rigidity to provide a support with a stable configuration. Preferred materials would also have a texture and resilience which would reduce irritation or trauma to the tissue of the body part supported by the wedge 56.

The support wedge 56 may be an inexpensive, sterile, disposable foam having a non-porous enclosure 55. The enclosure 55 may be made from materials including, but not limited to, polyethylene or vinyl resins. Alternatively, the support wedge 56 may be non-porous to aid cleaning of the support wedge 56 and to permit sterilization and reuse of the support wedge 56.

The tray 10 and cover 34 may be formed from materials, including but not limited to injection molded plastic, stamped metal or coated metal, to provide an inexpensive, sterile, disposable tray 10 and cover 34. Alternatively, reusable trays 10 and covers 34 may be made from materials, including but not limited to heat or radiation resistant plastics and stainless steel, that can be sterilized by conventional methods exemplified by autoclaving or gamma radiation treatment. The plastics include, but are not limited to, polycarbonate, polyphenylene ether and nylon.

Figure 5:
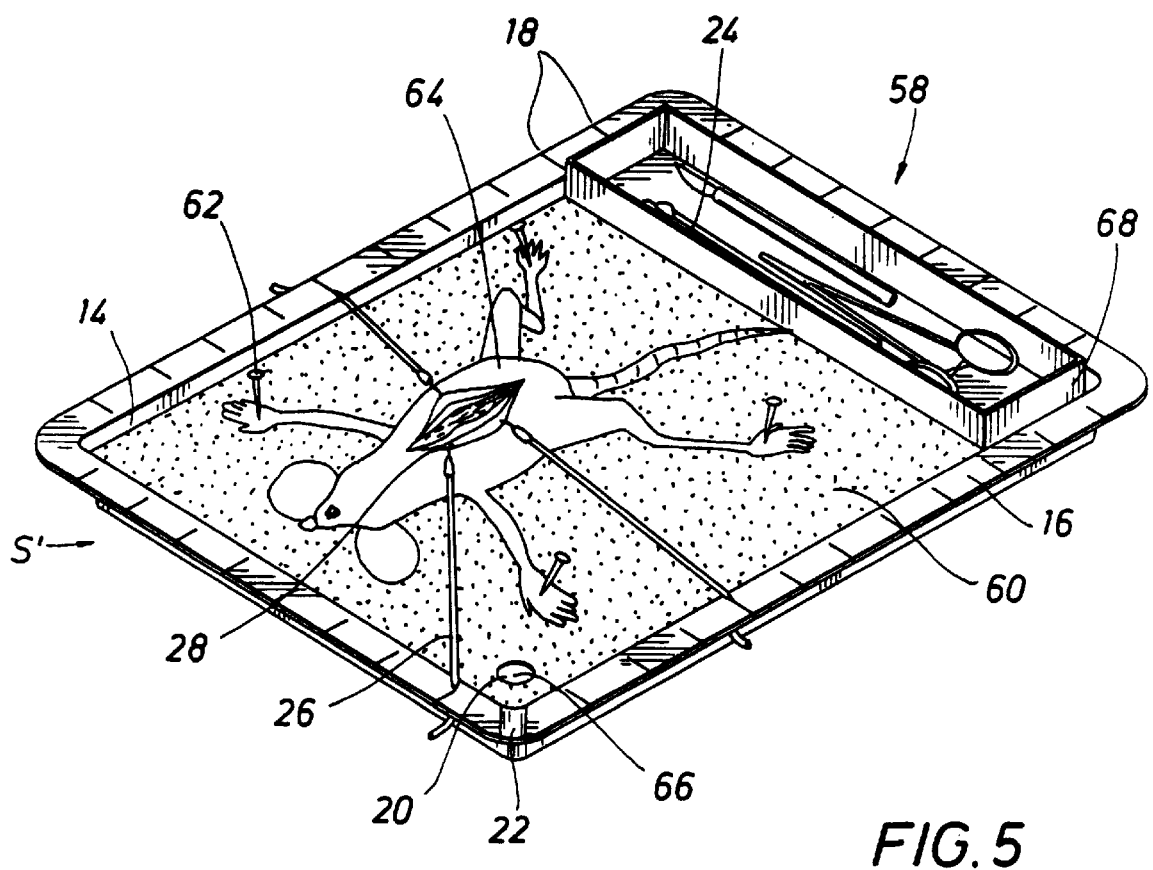
FIG. 5 is a perspective view of a surgical restraint system for use in a dissection kit.

As shown in FIG. 5, another embodiment according to the present invention is a surgical restraint system for use in a dissection kit designated as S'. The dissection kit S' includes a tray 10 as previously described.

As shown in FIG. 5, the kit S' includes an insert 60 which is sized and shaped to fit into a portion of the well of tray 10. The insert 60 is made of a material capable of receiving pins or needles 62 or other conventional immobilizing devices to hold a dissection specimen 64, for example a mouse, which may also be provided as part of the kit S'. The insert 60 may be made of, for example, wax. The insert 60 has a drain opening 66 placed to be coincident or at least partially overlapping with the drain opening 20 in tray 10. The insert drain opening 66 and the tray drain opening 20 permit fluids from the specimen 64 and any irrigation fluids to be safely directed into an appropriate disposal container.

As shown in FIG. 5, the tray 10 in the dissection kit S' may have a spout 22, formed in a portion of flange 16, in addition to the drain opening 20 or as an alternative to the drain opening 20. The spout 22 may be used to aid discharging accumulated fluids into an appropriate disposal container.

The dissection kit S' may also provide a tool bin 68 sized and shaped to fit into a portion of the well of tray 10. The tool bin 68 may be used to hold dissection equipment including, but not limited to, a scalpel, scissors, tongs, and retractor stay 24. The dissection kit 58 may also be provided with a cover 34 (FIG. 2) as previously described.

Figure 6:
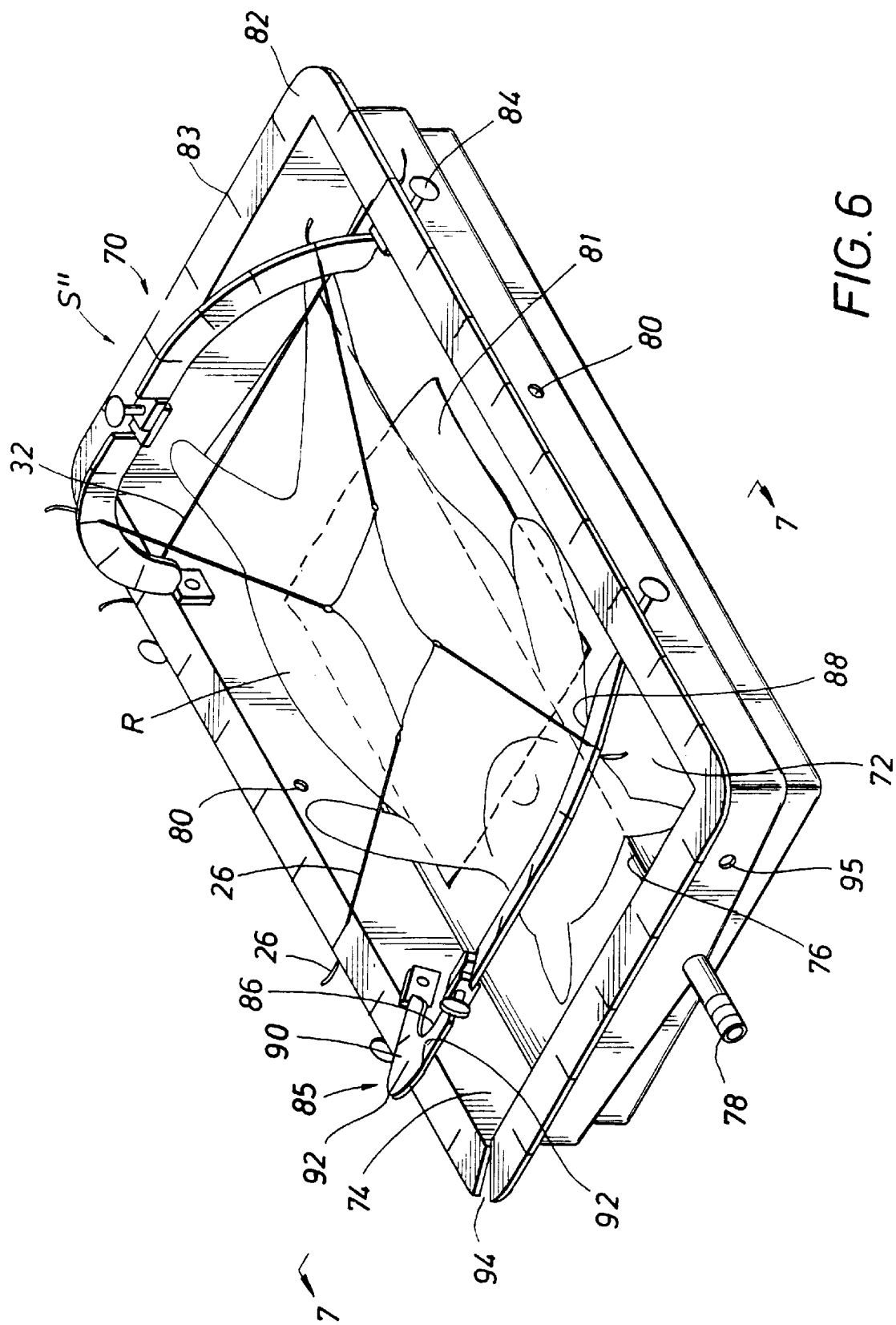
FIG. 6 is a perspective view of a surgical restraint system restraining a small animal during a surgical procedure.
Figure 7:
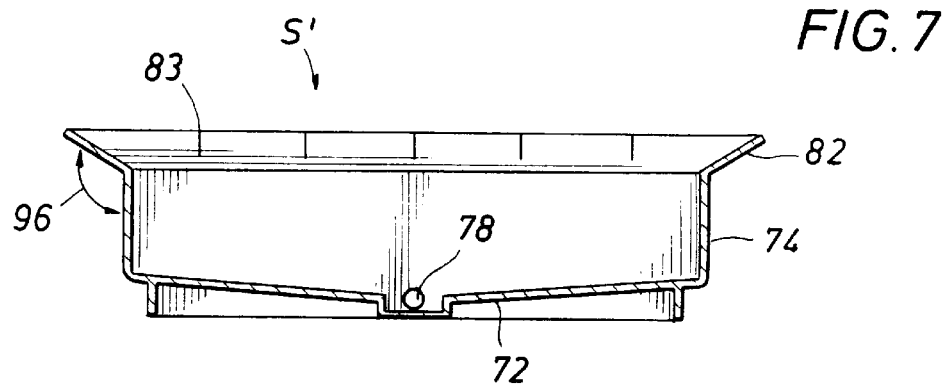
FIG. 7 is a side elevational view along lines 6—6 of the surgical restraint system shown in FIG. 6.

Another embodiment of the surgical restraint system of the present invention, generally referred to as S", is shown in FIGS. 6 and 7. This embodiment of the surgical restraint system S" performs several functions including, but not limited to, positioning an animal, immobilizing the animal and providing steady and constant retraction. The surgical restraint system S" includes a tray 70 adapted to receive a small animal R, for example a rabbit (FIG. 6). Tray 70 has a bottom member 72 from which a wall 74 extends to form a well to receive a small animal R and fluids associated with surgery or dissection.

The bottom member 72 typically has a peripheral edge from which a peripheral wall 74 extends to form a well in the tray 70. As previously stated with respect to the tray 10 of the surgical restraint system S, the tray 70 may also have alternative shapes and configurations.

The bottom member 72 is preferably declined towards a centerline 76 which forms a longitudinal midline in a rectangular tray as shown in FIG. 6. The midline is typically the lowest section of the bottom member 72 and is generally coincident with a drain 78. The inclined bottom member 72 aids in directing surgical fluids from the interior of tray 70 through the drain 78 into a suitable collection and disposal container (not shown). The inclination in the bottom member 72 may also aid in positioning the small animal for surgery, typically on its back or stomach.

Figure 8:
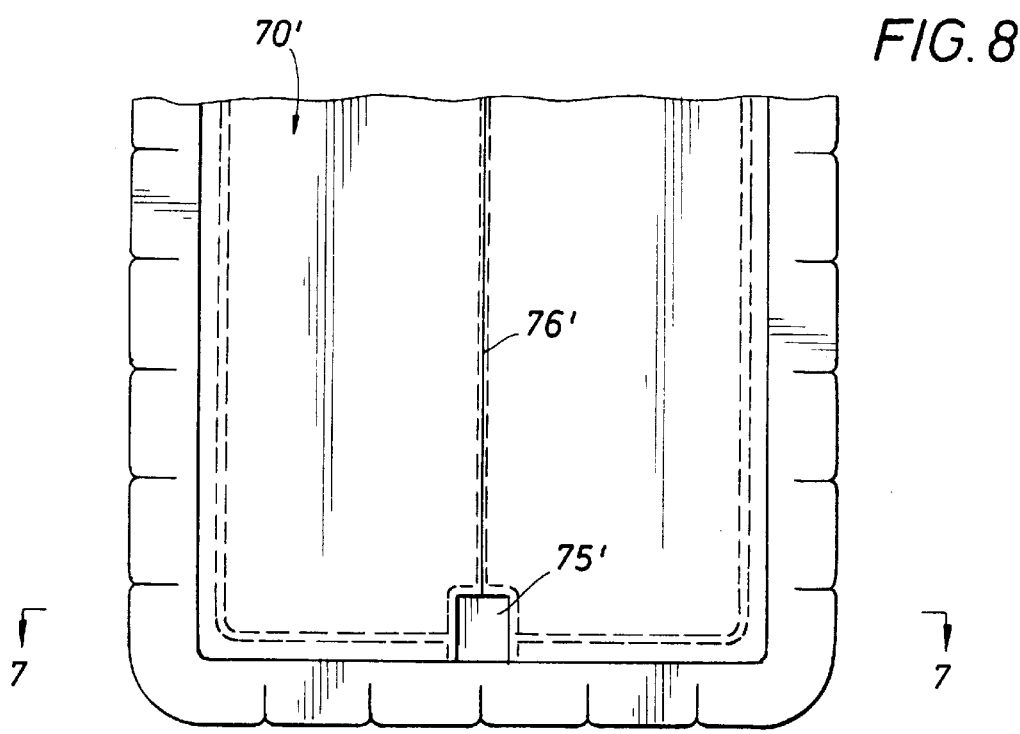
FIG. 8 is a partial plan view of an alternative embodiment of the tray.
Figure 9:
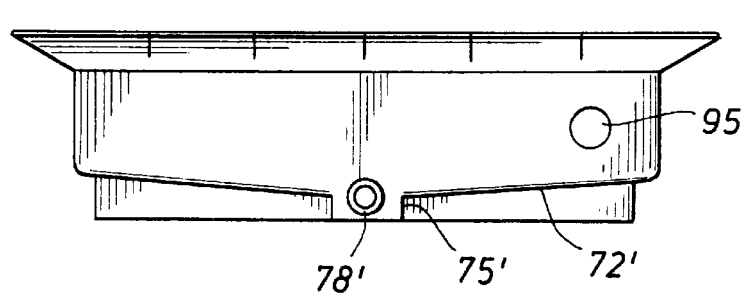
FIG. 9 is a sectional view taken along lines 9—9 of FIG. 8.

An alternative embodiment of the tray 70' and the drain 78' is shown in FIGS. 8 and 9. In this embodiment, the tray 70' includes a recessed area 75' at one end of the bottom member 72' along the midline 76'. Preferably, a drain or drain opening 78' in the recessed area 75' extends through the wall to facilitate the draining and collection of surgical fluids. The drain opening 78' may be a threaded hole for threadably connecting a drain.

Referring to FIG. 6, the peripheral wall 74 contains a plurality of holes 80 and a flange 82 extends from an upper perimeter of wall 74. Similar to the surgical restraint system S, the flange 82 also contains a plurality of notches 83 adapted to receive an elongated member 26 of a surgical retractor stay 24 or of a restraint stay 32. As shown in FIG. 7, the flange 82 typically has a low profile which may be concave, as shown by the arrow 96 in FIG. 7, to increase accessibility of the stays 24, 32 for ease of placement. The surgical restraint system S" may be adapted to receive all variations of the stays 24, 32 as described above for use with surgical restraint system S.

The wall holes 80 are adapted to receive screws or pins 84 which secure arms 85. The arms 85 may be integrally formed as one piece or arm 85 may be assembled from arm segments 86 and 88, as shown in FIG. 6. The arm segments 86, 88 may be joined together with a screw 84 which allows movement of the arm segments 86, 88 in unison. Alternatively, the arm segments 86, 88 may remain unjoined and moveable independently of one another. The arm segments 86, 88 are rotatably moveable when the screws 84 are loosened and may be held in a relatively fixed position by tightening the screws 84.

As shown in FIG. 6, the arm segments 86, 88 typically have a flange 90 with a plurality of notches 92. The notches 92 generally resemble and function in a similar manner as the notches 18 in the surgical restraint system S, as shown in FIG. 1.

As shown in FIGS. 6 and 7, the tray flange 82 preferably has a slot 94 adapted to receive an electrical cord to provide power to a heating pad 81 inserted into the well of tray 70. The slot 94 may also be used as a spout to pour accumulated fluids into a collection and disposal container (not shown). Alternatively, the peripheral wall 74 may include an opening 95 in addition to or in place of slot 94 to allow an electrical cord (not shown) for a heating pad 81 to pass, as shown in FIGS. 6 and 9.

The bottom surface of tray 70 may have a ridge or rib, as shown in FIG. 3 for tray 10, which may provide increased structural rigidity of tray 70. The cover 34, as shown in FIG. 2 for tray 10, may be attached to flange 82 of tray 70.

The tray 70 and arms 85 may be formed by conventional methods including, but not limited to, injection molding of plastic materials to provide an inexpensive sterile, disposable tray 70 and arms 85. Alternatively, reusable trays 70 and arms 85 may be made from materials including, but not limited to, heat or radiation resistant plastics and stainless steel that can be sterilized by conventional methods.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed is:

1. A surgical restraint system for use in surgery comprising:
    a tray having a well for receiving a portion of a body and for containing fluids accumulating during the surgery;
    a flange extending from the well for receiving a portion of a restraint, the flange having a plurality of notches; and
    a stay adapted to be received in the notches.

2. The system of claim 1, wherein the tray well is formed from a bottom member and walls extending from the bottom member.

3. The system of claim 1, further comprising an opening in the well for removal of the fluids accumulating during surgery.

4. The system of claim 1, wherein the bottom member further comprises a textured surface.

5. The system of claim 1, further comprising a pouring spout formed in the flange for discharging the accumulated fluids.

6. The system of claim 1, further comprising a snap-on cover having a lip with a recess to receive the flange.

7. The system of claim 1, wherein the stay includes an elongated member and a hook member attached to the elongated member.

8. The system of claim 7, wherein the elongated member is elastic.

9. The system of claim 7, wherein the elongated member has enlarged diameter sections.

10. The system of claim 7, wherein the elongated member is ribbed.

11. The system of claim 1, wherein the flange is concave.

12. The system of claim 1, further comprising a hole for receiving an electric power cable in one of the walls.

13. The system of claim 1, further comprising a heating pad.

14. The system of claim 1, wherein the tray comprises a material selected from the group consisting of polycarbonate, polyphenylene ether and nylon.

15. A surgical restraint system for use in a dissection kit comprising:

a tray having a bottom member and walls extending from the bottom member, the bottom member and walls forming a well for receiving a dissection specimen and for containing fluids accumulating during the dissection;

a notched flange extending from the walls for receiving a portion of a stay; and an insert in the well for receiving immobilizing devices for piercing and securing the specimen.

16. The system of claim 15, further comprising a dissection specimen.

17. The system of claim 15, further comprising:

an opening in the bottom member; and an opening in the insert, wherein the opening in the bottom member and the opening in the insert at least partially overlap to discharge the fluids from the well.

18. The system of claim 15, further comprising a pouring spout formed in the flange for discharging the fluids accumulating during dissection.

19. The system of claim 15, further comprising a snap-on cover having a lip with a recess to receive the flange.

20. The retractor system of claim 15, further comprising a surgical retractor stay having an elongated member and a hook member attached to the elongated member.

21. The system of claim 20, wherein the elongated member is elastic.

22. The system of claim 20, wherein the elongated member has enlarged diameter sections.

23. The system of claim 20, wherein the elongated member is ribbed.

24. The system of claim 15, wherein the flange is concave.

25. The system of claim 15, wherein the tray comprises a material selected from the group consisting of polycarbonate, polyphenylene ether and nylon.

26. A surgical restraint system for use in surgery comprising:

a tray having a well for receiving a small animal or portion of a body and for containing fluids accumulated during surgery, the well having a plurality of holes;

a flange extending from the well for receiving a portion of a restraint, the flange having a plurality of notches, an arm adapted to be attached to at least one hole; and a stay having an elongated member adapted to be received in the notches.

27. The system of claim 26, wherein the arm has a flange having a plurality of notches for receiving the elongated member.

28. The system of claim 26, wherein the tray well has a bottom member, the bottom member being sloped.

29. The system of claims 28, wherein the bottom member further comprises a textured surface.

30. The system of claim 26, further comprising a slot in the tray flange adapted to receive an electrical cord.

31. The system of claim 27, wherein the arm further comprises two arm segments adapted to be reversibly coupled.

32. The system of claim 26, wherein the elongated member is elastic.

33. The system of claim 26, wherein the elongated member has enlarged diameter sections.

34. The system of claim 26, wherein the elongated member is ribbed.

35. The system of claim 26, further comprising a hole for receiving an electric power cable in one of the walls.

36. The system of claim 26, further comprising a heating pad.

37. The system of claim 26, herein the tray comprises a material selected from the group consisting of polycarbonate, polyphenylene ether and nylon.

* * * * *